(12) United States Patent
Qiu

(10) Patent No.: US 9,353,052 B2
(45) Date of Patent: May 31, 2016

(54) FLUORINATED OLIGOMERS HAVING PENDANT BROMINE-CONTAINING MOIETIES

(75) Inventor: Zai-Ming Qiu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 80 days.

(21) Appl. No.: 13/988,380

(22) PCT Filed: Dec. 6, 2011

(86) PCT No.: PCT/US2011/063370
§ 371 (c)(1),
(2), (4) Date: May 20, 2013

(87) PCT Pub. No.: WO2012/082451
PCT Pub. Date: Jun. 21, 2012

(65) Prior Publication Data
US 2013/0253221 A1  Sep. 26, 2013

Related U.S. Application Data

(60) Provisional application No. 61/424,146, filed on Dec. 17, 2010, provisional application No. 61/424,107, filed on Dec. 17, 2010, provisional application No. 61/424,330, filed on Dec. 17, 2010, provisional application No. 61/424,153, filed on Dec. 17, 2010.

(51) Int. Cl.
| | |
|---|---|
| *C07C 313/04* | (2006.01) |
| *C08F 214/18* | (2006.01) |
| *C08F 8/04* | (2006.01) |
| *C08F 8/20* | (2006.01) |

(52) U.S. Cl.
CPC .................. *C07C 313/04* (2013.01); *C08F 8/04* (2013.01); *C08F 8/20* (2013.01); *C08F 214/18* (2013.01); *C08F 214/182* (2013.01)

(58) Field of Classification Search
None
See application file for complete search history.

(56) References Cited

U.S. PATENT DOCUMENTS

| | | | |
|---|---|---|---|
| 3,326,928 A | 6/1967 | Mattson | |
| 3,420,877 A | 1/1969 | Pavlik | |
| 6,624,328 B1 | 9/2003 | Guerra | |
| 2007/0142563 A1 | 6/2007 | Yandrasits | |
| 2007/0185220 A1 | 8/2007 | Lochhaas | |
| 2010/0292408 A1 | 11/2010 | Komatsu | |

FOREIGN PATENT DOCUMENTS

| | | | |
|---|---|---|---|
| CN | 101693751 | * | 4/2010 |
| WO | 98/06758 | * | 2/1998 |
| WO | WO 2012-082454 | | 6/2012 |
| WO | WO 2012-082546 | | 6/2012 |
| WO | WO 2012-082695 | | 6/2012 |
| WO | WO 2012-082703 | | 6/2012 |

OTHER PUBLICATIONS

Database CAPLUS Chemical Abstracts Service, Columbus, Ohio, US; Database Accession No. 2010:482117, Abstract of CN 101693751, Gao et al., Shandong Dongyue Shenzhou New Material Co., Ltd., Peop. Rep. China, Apr. 14, 2010.*
Machine Translation of CN 101693751.*
Database CAPLUS Chemical Abstracts Service, Columbus, Ohio, US; Database Accession No. 2010:694696, Abstract of Tang et al., Huaxue Xuebao (2010), 68(8).*
Harzdorf, "Uber Perfluoralkansulfinsauren", J. Liebigs Ann. Chem. 1973, pp. 33-39.
Huang, "Perfluoroalkylation of aromatics", Chinese J. Chem., 1993, vol. 11, No. 3, 272-279.
Huang, "Reaction of perfluoroalkanesulfonyl halide", "The reactions of perfluoroalkanesulfonyl bromide with a, p-unsaturated esters and chemical conversions of the products", Acat Chim. Sinica, 1989, No. 4, pp. 376-384.
Huang, "Reactions to Perfluoroalkanesulfonyl Bromide", 1986, No. 6, pp. 881-884.
Huang, "Studies on deiodo-sulfination Part. II", "The reactions of perfluoroalkanesulfinates with halogen and halogen acids and a new method for the synthesis of perfluorosulfonic acid", Journal of Fluorine Chemistry, Jun. 1983, vol. 23, No. 3, pp. 229-240.
Huang, "The reaction of perf luoroalkanesulfonyl halides", "Preparation and reactions of trifluoromethanesulfonyl bromide", Chinese J. Chem., 1992, vol. 10 No. 3, pp. 268-273.
Huang, "The reaction of perfluoroalkanesulfonyl halides", Chinese J. Chemistry, 1992, vol. 10, No. 3, pp. 274-277.
Huang, "The reactions of perfluoro-and\a\,\a\-dichloropolyfluoroalkanesulfinates", Acta Chimica Sinica, 1987, vol. 45, No. 5, pp. 445-449.
Ratcliffe, "Some Perfluoroalkylsulfinyl Halides, R,S(O)X. New Preparations of Trifluoromethylsulfur Trifluoride", J. Am. Chem. Soc., Mar. 1968, vol. 90, No. 20, pp. 5403-5408.
International Search Report for PCT International Application No. PCT/US2011/063370, Mailed Jul. 31, 2012, 4 pages.

* cited by examiner

*Primary Examiner* — Karl J Puttlitz
(74) *Attorney, Agent, or Firm* — Julie Lapos-Kuchar

(57) ABSTRACT

Described herein is an oligomer having a pendant bromine-containing moiety according to formula II and/or formula III; and combinations thereof; wherein $X_1$, $X_2$, and $X_3$ are each independently selected from F, Cl, H, and $CF_3$; R is a linear or branched linking group, which may be saturated or unsaturated, substituted or unsubstituted, and may comprise a heteroatom; each $Z_1$ and $Z_2$ is independently selected from F and $CF_3$; n is 0 or 1; q is 0 or 1; and m is at least 2.

9 Claims, No Drawings

FLUORINATED OLIGOMERS HAVING PENDANT BROMINE-CONTAINING MOIETIES

CROSS REFERENCE TO RELATED APPLICATIONS

This application claims priority to U.S. Provisional Application Nos. 61/424,146, 61/424,107, 61/424,330, and 61/424,153, all filed Dec. 17, 2010, the disclosures of which are incorporated by reference in their entirety herein.

TECHNICAL FIELD

The present disclosure relates to fluorinated oligomers having pendant bromine-containing moieties and methods of making.

SUMMARY

There is a desire to identify new fluorinated materials that can enable the ability to change the molecular weight or architecture (e.g., linear or branching) of a polymer. It is also desirable to find compositions that may improve the processing of fluoropolymer polymerization (e.g., by reducing processing temperatures) and/or may improve the finished properties (such as performance, e.g., thermal stability, mechanical stability, chemical stability and/or durability) of a polymerized fluoropolymer and/or fluoropolymer coating.

In one aspect, an oligomer is provided wherein the oligomer comprises a repeating unit selected from the group consisting of:

(i) a fluorinated poly(sulfonyl bromide) of Formula (II):

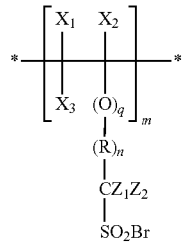

(ii) a fluorinated polybromide of Formula (III)

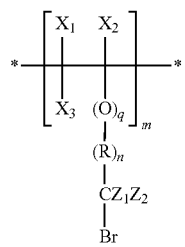

(iii) and combinations thereof;
wherein each $X_1$, $X_2$, and $X_3$ are each independently selected from F, Cl, H, and $CF_3$; R is a linear or branched linking group, which may be saturated or unsaturated, substituted or unsubstituted, and may comprise a heteroatom; each $Z_1$ and $Z_2$ is independently selected from F and $CF_3$; n is 0 or 1; q is 0 or 1; and m is at least 2.

In another aspect, a method for making a fluorinated poly(sulfonyl bromide) oligomer is provided comprising: (i) providing a polysulfinate oligomer comprising a repeating unit according to Formula I:

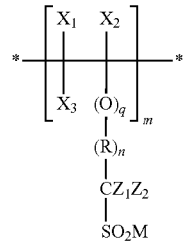

wherein each $X_1$, $X_2$, and $X_3$ are independently selected from F, Cl, H, and $CF_3$; R is a linear or branched linking group, which may be saturated or unsaturated, substituted or unsubstituted, and may comprise a catenary heteroatom; each $Z_1$ and $Z_2$ is independently selected from F and $CF_3$; n is 0 or 1; q is 0 or 1; m is at least 2 and M is a cation; and (ii) brominating the polysulfinate oligomer according to Formula I.

In yet another aspect, another method for making a fluorinated polybromide oligomer is described comprising: (i) providing a polysulfinate oligomer comprising a repeating unit according to Formula I:

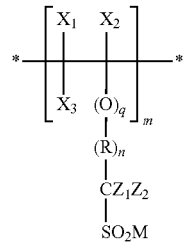

wherein $X_1$, $X_2$, and $X_3$ are each independently selected from F, Cl, H, and $CF_3$; R is a linear or branched linking group, which may be saturated or unsaturated, substituted or unsubstituted, and may comprise a catenary heteroatom; each $Z_1$ and $Z_2$ is independently selected from F and $CF_3$; n is 0 or 1; q is 0 or 1; m is at least 2; and M is a cation; (ii) brominating the sulfinate oligomer according to Formula I; and (iii) introducing an energy source.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more;
"and/or" is used to indicate one or both stated cases may occur, for example A and/or B includes, (A and B) and (A or B);
"linking group" refers to a divalent linking group. In one embodiment, the linking group includes at least 1 carbon atom (in some embodiments, at least 2, 4, 8, 10, or even 20 carbon atoms). The linking group can be a linear or branched, cyclic or acyclic structure, that may be saturated or unsaturated, substituted or unsubstituted, and optionally contains one or more hetero-atoms selected from the group consisting of sulfur, oxygen, and nitrogen, and/or optionally contains one or more functional groups selected from the group consisting of ester, amide, sulfonamide, carbonyl, carbonate, urethane, urea, and carbamate;

"poly" is used as a prefix herein to indicated more than 1 repeated unit, e.g., more than 2, more than 3, more than 4, more than 6, more than 8, more than 10, etc.; and "sulfinate" is used herein to refer interchangeably to compounds comprising sulfinic acids and salts thereof.

Also,

as used herein, refers to a segment Q (e.g., a monomer) in a compound, such as in an oligomer. In this instance, "p" refers to the number of times segment Q is repeated in the compound and may include either random or block oligomer configurations. For example, in

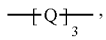

the compound would include block co-oligomer and random co-oligomer configurations, for example, -QQQYYY— as well as -QYQYQY— or —YQQYQY—.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 3, at least 4, at least 6, at least 8, at least 10, at least 25, at least 50, at least 100, etc.).

The present disclosure is directed to oligomers having at least two pendant bromine-containing moieties and methods of making them. As used herein a pendant bromine-containing moiety refers to a side group off of the main oligomer chain that comprises a terminal bromine atom, specifically, a bromide, or a sulfonylbromide.

The oligomers of the present disclosure comprise a repeating unit as shown in Formulas II and III below:

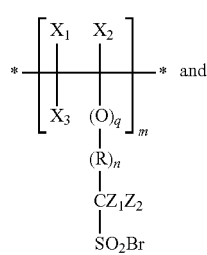

and

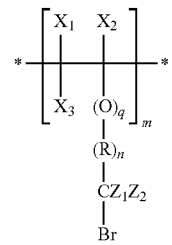

wherein each $X_1$, $X_2$, and $X_3$ are independently selected from F, Cl, H, and $CF_3$; R is a linear or branched linking group, which may be saturated or unsaturated, substituted or unsubstituted, and optionally comprises at least one catenary heteroatom (such as O, N, and/or S); each $Z_1$ and $Z_2$ is independently selected from F and $CF_3$; n is 0 or 1; q is 0 or 1; and m is at least 2, 3, 4, 5, 10, 20, etc.

R may be non-fluorinated, partially fluorinated, or perfluorinated. In some embodiments, the hydrogen atom is replaced with a halogen other than fluorine, such as a chlorine. R may or may not comprise double bonds. R may be substituted or unsubstituted, linear or branched, cyclic or acyclic, and may optionally comprise a functional group (e.g., esters, ethers, ketones, amines, etc.).

In one embodiment of the compound according to Formulas II or III, n+q is at least 1 (in other words, q and n are not both 0).

In one embodiment of the compound according to Formulas II or III, the $X_1$, $X_2$, and $X_3$ are all F and R is a perfluorinated alkylene (in other words, a divalent perfluorinated carbon that may be linear or branched) and may comprise 2, 3, 4, 6, 8, 10, 12, 18, or even 20 carbon atoms.

In one embodiment of the compound according to Formulas II or III, R is selected from: $-(CH_2)_a-$, $-(CF_2)_a-$, $-(CF_2)_a-O-(CF_2)_b-$, $-(CH_2)_a-(CF_2)_b-$, $-(CF_2)_a-O-(CF_2CF(CF_3))_b-$, $-(CF_2)_a-[O-(CF_2)_b]_c-$, $-[(CF_2)_a-O-]_b-[(CF_2)_c-O-]_1$, and combinations thereof, wherein a, b, c, and d are independently at least 1, 2, 3, 4, 10, 20, etc.

In some embodiments, the oligomers of the present disclosure are highly fluorinated, meaning that 80%, 90%, 95%, or even 99% of the C—H bonds on the oligomer are replaced by C—F bonds, excluding the terminal bromine atom (—Br or —$SO_2$Br) of the pendant bromine-containing moiety.

An oligomer having C—F bonds and no C—H bonds on the oligomer are referred to herein as a perfluorinated oligomer. A perfluorinated oligomer of the present disclosure (i.e., Formulas II and III) may comprise partially fluorinated or nonfluorinated end groups, depending on the reaction scheme used to generate the oligomer. For example, in Formulas II and III the end group is represented with an "*" and the endgroups may not be perfluorinated. The end group "*" may be independently selected from H, F, an alkyl group, a partially fluorinated alkyl group, or a perfluorinated alkyl group.

In other embodiments, the oligomers of the present disclosure (i.e., Formulas II and III) are partially fluorinated, meaning that the oligomer contains at least one hydrogen atom connected to a carbon in the oligomer and also contains at least one fluorine atom connected to a carbon in the oligomer.

Exemplary oligomers according to Formulas II and III include: $-[CF_2CF(OCF_2CF_2SO_2Br)]-$, $-[CF_2CF(O(CF_2)_4SO_2Br)]-$, $-[CF_2CF(OCF_2CF(CF_3)SO_2Br)]-$, $-[CF_2CF(OCF_2CF(CF_3)OCF_2CF_2SO_2Br)]-$, $-[CH_2CH(CF_2CF_2SO_2Br)]-$, $-[CH_2CH((CF_2)_4SO_2Br)]-$, —[CF$_2$CF(OCF$_2$CF$_2$Br)]—, —[CF$_2$CF(O(CF$_2$)$_4$Br)]—, —[CF$_2$CF(OCF$_2$CF(CF$_3$)Br)]—, —[CF$_2$CF(OCF$_2$CF(CF$_3$)OCF$_2$CF$_2$Br)]—, —[CH$_2$CH(CF$_2$CF$_2$Br)]—, —[CH$_2$CH((CF$_2$)$_3$Br)]—, —[CH$_2$CH((CF$_2$)$_4$Br)]—, and combinations thereof.

In one embodiment, the oligomers of the present disclosure may be made by providing a sulfinate oligomer according to Formula I:

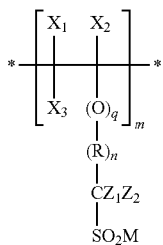

wherein each $X_1$, $X_2$, and $X_3$ are independently selected from F, Cl, H, and CF$_3$; R is a linear or branched linking group, which may be saturated or unsaturated, substituted or unsubstituted, and optionally comprises at least one catenary heteroatom (such as O, N, and/or S); each $Z_1$ and $Z_2$ is independently selected from F and CF$_3$; n is 0 or 1; q is 0 or 1; and m is at least 2.

In one embodiment, n+q is at least 1 (in other words, n and q are not both 0).

In one embodiment, R is selected from: —(CH$_2$)$_a$—, —(CF$_2$)$_a$—, —(CF$_2$)$_a$—O—(CF$_2$)$_b$—, —(CH$_2$)$_a$—(CF$_2$)$_b$—, —(CF$_2$CF(CF$_3$)O)$_a$— and —(CF$_2$)$_a$—[O—(CF$_2$)$_b$]$_c$—, —[(CF$_2$)$_a$—O—]$_b$—[(CF$_2$)$_c$—O—]$_d$, —[(CF$_2$)$_a$—O—]$_b$—[(CF$_2$CF(CF$_3$)O)$_c$—]$_d$—, and combinations thereof, wherein a, b, c, and d are independently at least 1.

The cation, M, in Formula I may comprise H', an inorganic cation including, but not limited to: Na$^+$, Li$^+$, Cs$^+$, Ca$^{+2}$, K$^+$, NH$_4^+$, Mg$^{+2}$, Zn$^{+2}$, and Cu$^{+2}$, and/or an organic cation including, but not limited to N(CH$_3$)$_4^+$, NH$_2$(CH$_3$)$_2^+$, N(CH$_2$CH$_3$)$_4^+$, NH(CH$_2$CH$_3$)$_3^+$, NH(CH$_3$)$_3^+$, and (CH$_3$CH$_2$CH$_2$CH$_2$)$_4$P$^+$.

Exemplary sulfinate oligomers according to Formula I include: —[CF$_2$CF(OCF$_2$CF$_2$SO$_2$M)]-, —[CF$_2$CF(O(CF$_2$)$_4$SO$_2$M)]-, —[CF$_2$CF(OCF$_2$CF(CF$_3$)SO$_2$M)]-, —[CF$_2$CF(OCF$_2$CF(CF$_3$)OCF$_2$CF$_2$SO$_2$M)]-, —[CH$_2$CH(CF$_2$CF$_2$SO$_2$M)]-, —[CH$_2$CH((CF$_2$)$_3$SO$_2$M)]-, —[CH$_2$CH((CF$_2$)$_4$SO$_2$M)]-, and combinations thereof, where M is a cation as defined above.

Exemplary sulfinate oligomers are disclosed in U.S. Prov. Appl. Nos. 61/424,146 (Guerra et al.), 61/424,153 (Guerra et al.), and 61/424,107 (Qiu et al.). For example, Guerra et al. (U.S. Prov. Appl. No. 61/424,146) discloses methods of making highly fluorinated sulfinic acid oligomers and co-oligomers, and salts thereof. In making the sulfinic acid oligomer, a highly fluorinated vinyl sulfonyl halide is oligomerized using an initiator to provide a highly fluorinated oligomeric sulfonyl halide. This sulfonyl halide is then reduced to form the highly fluorinated sulfinate oligomer. Qiu et al. (U.S. Prov. Appl. No. 61/424,107) discloses partially fluorinated polysulfinic acids and salts thereof along with methods of making them. Qiu et al. discloses oligomerizing a halofluoroalkene monomer with a sulfinating agent to produce the partially fluorinated polysulfinic acid or salt thereof.

In the present disclosure, the sulfinate oligomers as represented by Formula I may be brominated to form oligomers having pendant bromine-containing moieties. The oligomers having pendant bromine-containing moieties, including the poly(sulfonyl bromide) and polybromide, of the present disclosure are represented by Formulas II and III, above.

Oligomers having pendant bromine-containing moieties may be obtained by contacting the sulfinate oligomer of Formula I with a brominating agent. Brominating agents as known in the art may be used to brominate the sulfinate oligomer. Such brominating agents include: diatomic bromine, hypobromite, hypobromous acid, and combinations thereof.

By adjusting the reaction conditions as disclosed in the present disclosure, not only can the bromine-containing product can be favored (i.e., result in a high yield), but the nature of the pendent moiety and/or the ratio of brominated segments according to Formula II and III in an oligomer may be controlled. Furthermore, because the bromide-terminated pendent group is more stable than the sulfonyl bromide-terminated pendent group, using increased temperatures, electromagnetic radiation, and longer reaction times will generally favor the formation of the product comprising the bromine-terminated pendent group, as opposed to the sulfonyl bromide-terminated pendent group.

The amount of brominating agent used can be selected for partial or complete bromination. For example, 0.01 to 2, 0.05 to 1.5, or even 0.1 to 1.2 equivalents of brominating agent may be used per sulfinate. If complete conversion of the sulfinate moiety to the bromide or sulfonyl bromide moiety is desired, generally, at least 1 equivalent of brominating agent per sulfinate should be used, preferably, an excess of brominating agent per sulfinate should be used. If less than 1 equivalent of brominating agent per sulfinate is used, typically oligomers having pendent bromine-containing moieties and pendent sulfinate moieties are achieved.

In some embodiments, the brominating step is conducted in the presence of water or an organic solvent. Exemplary organic solvents include: an acid, such as acetic acid; an alcohol such as ethanol or isopropanol; polar aprotic solvents such as acetonitrile; halogenated solvents such as chloroform, dichloromethane, tetrachloromethane, or fluorinated solvents including hydrofluoroethers such as those sold under the trade designation "3M NOVEC" by 3M Co., St. Paul, Minn. Examples of hydrofluoroether solvents are C$_4$F$_9$OCH$_3$, C$_4$F$_9$OCH$_2$CH$_3$ and their azotrope or azotropic-like compositions with organic solvents. To assist in good conversion to the brominated oligomer, it is preferred that the solvent (e.g., water or an organic solvent) have high solubility to both the fluorinated polysulfinate oligomer and the brominating agent. In some embodiments, if the oligomer has pendent sulfonyl bromide moieties and the oligomer has limited or poor solubility in a chosen solvent, the formation of the pendent bromine-containing moiety, shown in Formula III, may not be favored.

In one embodiment that cation, M, of the sulfinate oligomer according to Formula I, can influence the selectivity of the reaction. For example, the cation may impact the solubility of the sulfinate oligomer according to Formula I in a solvent.

The brominating step may be conducted at a temperature of at least −20° C., −10° C., 0° C., 5° C., 10° C., 20° C., 23° C., 25° C., 30° C., 35° C., or even 40° C.; and at most 45° C., 50° C., 60° C., 75° C., 90° C., 100° C., or even 100° C. In some embodiments, the brominating step is conducted at room temperature. In some embodiments, the brominating step is conducted at 0° C. By adjusting the temperature during the brominating step, the fluorinated poly(sulfonyl bromide) or the fluorinated polybromide may be favored. For example, lower temperature (e.g., 0° C.) is preferred during the bromination reaction for making a fluorinated poly(sulfonyl bromide) oligomer; the fluorinated polybromide oligomer is generally the preferred product when higher temperatures (e.g., 100° C.) are used during the bromination reaction.

Exposure of the fluorinated poly(sulfonyl bromide) to additional energy can convert a poly(sulfonyl bromide) to a polybromide. In one embodiment, the brominated oligomer is exposed to heat following the bromination step. For example, if a heat energy source is used, typically the reaction is exposed to temperatures of 40° C. and above for 0.5 to 24 hours depending on the cation (M) of the sulfinate and the selected solvent.

In one embodiment, an electromagnetic-radiation source (or any source that is capable of breaking the S—Br bond of the sulfonyl bromide group) is used to provide additional energy. The electromagnetic-radiation source may be introduced during the brominating of the polysulfinate oligomer and/or may be used after brominating the sulfinate oligomer. Typically, the input of electromagnetic-radiation (i.e., additional energy) into the system, will result in favoring the formation of the polybromide oligomer.

Typically the electromagnetic radiation is in the form of visible irradiation (380-780 nm), ultraviolet (wavelengths of 10-400 nanometers), infrared, microwave, or gamma radiation. The use of electromagnetic radiation may require minutes to hours for completed conversion to the pendent bromine-containing moiety depending the selected source and the power of the source.

In addition to the formation of oligomers comprising pendent bromide and/or pendent sulfonyl bromide moieties, in some embodiments, the oligomers of the present disclosure may comprise additional pendent functional groups, such as segments according to Formula (IV):

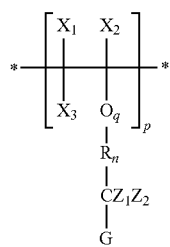

wherein each $X_1$, $X_2$, and $X_3$ are independently selected from F, Cl, H, and $CF_3$; R is a linear or branched linking group, which may be saturated or unsaturated, substituted or unsubstituted, and optionally comprises at least one catenary heteroatom; each Z1 and Z2 is independently selected from F and $CF_3$; q is 0 or 1; n is 0 or 1; p is at least 1; and G is F, a functionalized group, or a combination thereof, wherein the functionalized group is selected from the group consisting of —$SO_2M$, —$SO_3M$, —$SO_2NR^1R^2$, —$CO_2M$, —$CO_2R^1$, —$CH_2OR^1$, —$SO_2F$, —$SO_2Cl$, H, I, and combinations thereof, wherein M is a cation and $R^1$ and $R^2$ are independently selected from a linear or branched linking group, which may be saturated or unsaturated, substituted or unsubstituted, and optionally comprises catenary heteroatoms.

M may comprise $H^+$; inorganic cations including, but not limited to: $Na^+$, $Li^+$, $Cs^+$, $Ca^{+2}$, $K^+$, $NH_4^+$, $Mg^{+2}$, $Zn^{+2}$, and $Cu^{+2}$; and/or organic cations including, but not limited to $N(CH_3)_4^+$, $NH_2(CH_3)_2^+$, $N(CH_2CH_3)_4^+$, $NH(CH_2CH_3)_3^+$, $NH(CH_3)_3^+$, $((CH_3CH_2CH_2CH_2)_4)P^+$, and combinations thereof.

In one embodiment, n+q is at least 1.

In one embodiment, these segments comprising additional pendent functional groups may comprise at least 5, 10, 15, 20, 25, or even 30 mol %; and at most 40, 50, 60, 75, 80, or even 90 mol % versus the total functional groups present in the oligomer. In other words, the total functional groups would include the bromide-terminated pendent groups and those functional pendent groups at the end of the pendent group in segments according to Formula IV.

In one embodiment, these segments comprising additional pendent functional groups may be added to the polysulfinate oligomer prior to bromination. In another embodiment, these additional segments may be a result of incomplete bromination of the polysulfinate oligomer, resulting in an oligomer comprising both pendent sulfinate and pendent bromine-terminated functional groups. In another embodiment, these additional segments may be generated by partially converting —$SO_2M$, —$SO_2Br$, or —Br from the oligomer to different functional groups by selected reactions.

An oligomer comprising pendent groups having various functional groups, whether they are sulfonyl bromide and bromide moieties or sulfonyl bromide and sulfinate moieties or some other combination, can be advantageous. An oligomer comprising multiple different functional groups, may result in a compound having multiple reaction sites with different reactivity that are able to undergo reactions under different conditions. For example if an oligomer comprises two different functional groups, the first functional group may be used to initiate the polymerization at different conditions and to introduce a branched structure to a polymer, and the second functional group may be used as a crosslinking agent to further cross-link the polymer. Such exemplary compounds may reduce process steps and/or eliminate the extra co-monomer enabling lower cost, generating a unique polymer of coating structure having unique properties.

In one embodiment, additional monomers may be introduced into oligomer to adjust the properties of the resulting oligomer by co-oligomerization. The additional monomer(s) during the preparation of the fluorinated polysulfinate oligomer before bromination. For example additional monomers may be used to adjust the molecular weight or to change the hydrophobic/hydrophilic nature of the resulting product or specific functional groups for specific applications. In one embodiment, the additional monomers are introduced into the sulfinate oligomer prior to bromination.

In some embodiments, the oligomer of the present disclosure may further comprise a segment (or repeating unit) according to Formula IV:

(IV)

wherein Q is derived from a monomer and p is at least 1, 2, 3, 4, 5, 10, 20, etc. Generally, the amount of monomer is selected such that the ratio to the pendent bromine-containing moiety is from 1:9 or even 1:1.

The additional monomer may be selected from a non-fluorinated olefin, a partially fluorinated olefin, a perfluorinated olefin, and combinations thereof.

In one embodiment, the additional monomer is a compound selected from the following Formula: $CY_2$=$CY(R^1)$, wherein each Y is independently selected from H or F; and $R^1$ is selected from I, Cl, Br, F, H, $CH_3$, O—$R_f$-U and $R_f$-U wherein U=I, H, Br, F, $CH_2OH$, $CO_2R^1$, CN, $C(O)NR^1R^2$, $P(O)(OR^1)_2$, $OR^1$, $OCF_3$, $OC_3F_7$, and $R_f$ is a perfluorinated or partially fluorinated alkylene group optionally containing heteroatoms.

In another embodiment, the additional monomer may be selected from non-fluorinated bromo- or iodo-olefins.

Exemplary additional monomers include, ethylene, tetrafluoroethylene, propylene, hexafluoropropylene, vinyl chloride, vinyl fluoride, vinyl iodide, allyl iodide, a fluoroalkyl substituted ethylene, vinylidene fluoride, fluorinated alkyl vinyl ethers, fluorinated alkoxy vinyl ethers, bromotrifluoroethylene, chlorotrifluoroethylene, and combinations thereof.

Additional exemplary monomers include: $CF_3CH=CH_2$, $C_4F_9CH=CH_2$, $CF_3OCF=CF_2$, $C_3F_7OCF=CF_2$, $C_3F_7OCF_2CF(CF_3)OCF=CF_2$, $CF_3OCF_2CF_2CF_2OCF=CF_2$, $CH_2=CHCF_3$, $CH_2=CHCF_2CF_2CF_3$, $CF_2=CFOCF_2CF_2CO_2CH_3$, $CF_2=CFO(CF_2)_4CO_2CH_3$, $CF_2=CFOCF_2CF(CF_3)OCF_2CF_2CO_2CH_3$, $CF_2=CFOCF_2CF_2CF_2OCF_3$, $CH_2=CHCF_2CF_2COONH_2$, $CF_2=CFOCF_2CFOCF_2CF_2P(O)(OR)_2$, $CF_2=CFO(CF_2)_3I$, $CF_2=CFO(CF_2)_5CN$, $CH_2=CHCF_2CN$, $CH_2=CH(CF_2)_2CN$, $CF_2=CF(CF_2)_2CF_2Br$, $CHBr=CF_2$, $CF_2=CFO(CF_2)_5CH_2OH$, $CF_2=CFO(CF_2)_2Br$, $CH_2=CHCF_2CF_2—CH_2OH$, $CH_2=CH_1$, $CF_2=CH_1$, $CF_2=CF_1$, $CH_2=CHCH_2I$, $CF_2=CFCF_2I$, $CH_2=CHCF_2CF_2I$, $CH_2=CHCF_2CF_2CH_2CH_2I$, $CH_2—CH(CF_2)_4I$, $CH_2=CH(CF_2)_4—CH_2CH_2I$, $CH_2—CH(CF_2)_6I$, $CH_2—CH(CF_2)_6CH_2CH_2I$, $CF_2=CFCH_2CH_2I$, $CF_2=CFCF_2CF_2I$, $CF_2=CFOCF_2CF_2I$, $CF_2=CFOCF_2CF_2CH_2CH_2I$, $CF_2=CFOCF_2CF_2CF_2I$, $CF_2=CFOCF_2CF_2CF_2CH_2CH_2I$, $CF_2=CFOCF_2CF_2CH_2I$, $CF_2=CFOCF_2CF_2CF_2CH_2I$, $CF_2=CFCF_2OCH_2CH_2I$, $CF_2=CFO(CF_2)_3—OCF_2CF_2I$, $CH_2=CHBr$, $CF_2=CHBr$, $CH_2=CHCH_2Br$, $CF_2=CFCF_2Br$, $CH_2=CHCF_2CF_2Br$, $CF_2=CFOCF_2CF_2Br$, $CF_2=CFCl$, $CF_2=CFCF_2Cl$, and combinations thereof.

In one embodiment, the oligomer of the present disclosure may comprise even more additional (e.g., second, third, fourth, fifth, etc.) monomer segments selected from a non-fluorinated olefin, a partially fluorinated olefin, a perfluorinated olefin, and combinations thereof.

The resulting product of the present disclosure may be isolated and optionally purified by known methods. In one embodiment, the crude product is isolated from the aqueous reaction mixture by phase separation from the bottom layer of aqueous solution due to the higher density of highly fluorinated bromo-oligomers. In another embodiment, the crude solid is isolated by extracting with a solvent, such as halogenated solvent to remove insoluble inorganic impurity followed by the stripping out of solvent. Useful halogenated solvent are, for example, $CH_2Cl_2$, $CHCl_3$, $CCl_4$, $ClCH_2CH_2Cl$, $C_4F_9OCH_3$ and $C_4F_9OCH_2CH_3$.

In some embodiments further purification of the crude product is sometimes not necessary. The elimination of the purification step may reduce processing time and cost. If desired, the reaction mixture or crude product may be purified, for example, by repeated water washing and phase separation.

In one embodiment, resulting oligomers prepared according to the present disclosure may comprise a majority of segments corresponding to Formulas II and/or III. Wherein a majority means at least 50, 60, 70, 80, 90, or even 100% by weight of the final product comprises segments corresponding to Formulas II or III.

In one embodiment, the resulting oligomers prepared according to the present disclosure have a number average molecular weight of no more than 20,000 grams/mole, 15,000 grams/mole, 10,000 grams/mole, 5,000 grams/mole, 2,000 grams/mole, 1500 grams/mol, or even 1000 grams/mole.

Advantageously, the oligomer of the present disclosure comprises oligomers that have for example, at least 2, 3, 5, 7, or 10 bromine-containing moieties off of the oligomer chain.

The bromine-containing oligomer, especially the polysulfonyl bromide oligomer of the present disclosure may be useful as a reactive intermediate. The fluorinated poly(sulfonyl bromide) may be used as an initiator and chain transfer agent or brominating agent for radical reactions or polymerization reactions for polymers having fewer undesired unstable polar end-groups, and a crosslinking agent for fluoropolymers and coatings.

Advantageously, the compounds of the present disclosure may be useful as an initiator and/or crosslinking agent for polymers and coatings having improved thermal, chemical, and/or mechanical stability, and/or durability.

Exemplary Embodiments of the present disclosure include:

Embodiment 1. A composition comprising an oligomer comprising a repeating unit selected from the group consisting of:

Formula (II)

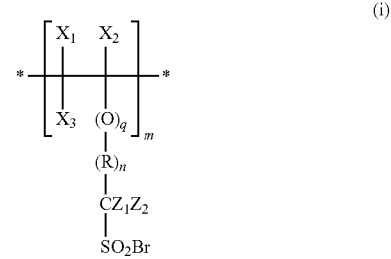

(i)

Formula (III)

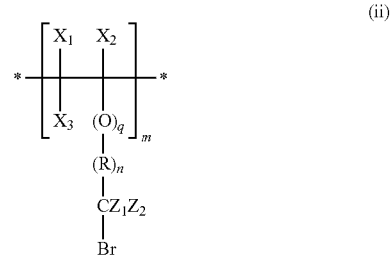

(ii)

(iii) and combinations thereof;

wherein $X_1$, $X_2$, and $X_3$ are each independently selected from F, Cl, H, and $CF_3$; R is a linear or branched linking group, which may be saturated or unsaturated, substituted or unsubstituted, and may comprise a catenary heteroatom; each $Z_1$ and $Z_2$ is independently selected from F and $CF_3$; n is 0 or 1; q is 0 or 1; and m is at least 2.

Embodiment 2. The composition of embodiment 1 further comprising a repeating unit of Formula (IV):

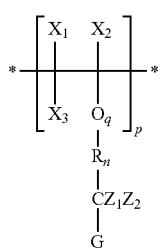

wherein each $X_1$, $X_2$, and $X_3$ are each independently selected from F, Cl, H, and $CF_3$; R is a linear or branched linking group, which may be saturated or unsaturated, substituted or unsubstituted, and may comprise catenary heteroatoms; each $Z_1$ and $Z_2$ is independently selected from F and $CF_3$; q is 0 or 1; n is 0 or 1; q+n is at least 1; p is at least 1; and G is F or a functionalized group, wherein the functionalized group is selected from the group consisting of —$SO_2M$, —$SO_3M$, —$SO_2NR^1R^2$, —$CO_2M$, —$CO_2R^1$, —$CH_2OR^1$, —$SO_2F$, —$SO_2Cl$, H, or I, wherein M is a cation and $R^1$ and $R^2$ are independently selected from a linear or branched linking group, which may be saturated or unsaturated, substituted or unsubstituted, and may comprise a catenary heteroatom.

Embodiment 3. The composition according to any one of the previous embodiments, further comprising a repeating unit:

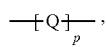

wherein Q is derived from a monomer and p is at least 1.

Embodiment 4. The composition according to embodiment 3, wherein the monomer is selected from a non-fluorinated olefin, a partially fluorinated olefin, a perfluorinated olefin, and combinations thereof.

Embodiment 5. The composition according to any one of embodiments 3-4, wherein the monomer is selected from the following Formula: $CY_2$=$CY(R^3)$, wherein each Y is independently selected from H, Cl or F; and $R^3$ is selected from I, Br, O—$R_f$-U, $R_f$-U wherein U=I, F, H, Br, $CH_2OH$, $CO_2R^1$, CN, $C(O)NR^1R^2$, $P(O)(OR^1)_2$, $OR^1$, $OCF_3$ or $OC_3F_7$, and $R_f$ is a perfluorinated or partially fluorinated alkylene group optionally containing O atoms.

Embodiment 6. The composition according to any one of embodiments 3-5 wherein the monomer is selected from: ethylene, tetrafluoroethylene, propylene, hexafluoropropylene, vinyl chloride, vinyl fluoride, a fluoroalkyl substituted ethylene, vinylidene fluoride, allyl iodide, fluorinated alkyl vinyl ethers, fluorinated alkoxy vinyl ethers, bromotrifluoroethylene, chlorotrifluoroethylene, $CF_3CH$=$CH_2$, $C_4F_9CH$=$CH_2$, $CF_3OCF$=$CF_2$, $C_3F_7OCF$=$CF_2$, $CF_2$=$CFOCF_2CF(CF_3)OCF_2CF_2CF_3$, $CF_2$=$CFOCF_2CF_2CF_2CN$, $CF_2$=$CFOCF_2CF_2CF_2CO_2CH_3$, $CF_2$=$CFOCF_2CF(CF_3)OCF_2CF_2CO_2CH_3$, $CF_2$=$CFOCF_2CF_2CF_2CH_2OH$, and $CF_2$=$CFOCF_2CF_2CF_2OCF_3$.

Embodiment 7. The composition according to any one of the previous embodiments, wherein the $X_1$, $X_2$, and $X_3$ are all F, n is 1, and R is a perfluorinated alkylene.

Embodiment 8. The composition according to any one of embodiments 1-6, wherein R is selected from: —$(CH_2)_a$—, —$(CF_2)_a$—O—$(CF_2)_b$—, —$(CF_2CF(CF_3)O)_a$— and —$(CF_2)_a$—[O—$(CF_2)_b]_c$—, —[$(CF_2)_a$—O$]_b$—[$(CF_2)_c$—O$]_d$—, —[$(CF_2)_a$—O$]_b$—[$(CF_2CF(CF_3)O)_c$—$]_d$—, and combinations thereof, wherein a, b, c, and d are independently at least 1.

Embodiment 9. A method for making a fluorinated polysulfonyl bromide oligomer comprising: (i) providing a polysulfinate oligomer comprising a repeating unit according to Formula I:

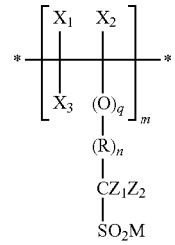

wherein $X_1$, $X_2$, and $X_3$ are each independently selected from F, Cl, H, and $CF_3$; R is a linear or branched linking group, which may be saturated or unsaturated, substituted or unsubstituted, and may comprise a catenary heteroatom; each $Z_1$ and $Z_2$ is independently selected from F and $CF_3$; n is 0 or 1; q is 0 or 1; and m is at least 2; and M is a cation; and (ii) brominating the polysulfinate oligomer according to Formula I.

Embodiment 10. A method for making a fluorinated polybromide oligomer comprising: (i) providing a polysulfinate oligomer comprising a repeating unit according to Formula I:

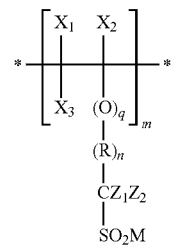

wherein $X_1$, $X_2$, and $X_3$ are each independently selected from F, Cl, H, and $CF_3$; R is a linear or branched linking group, which may be saturated or unsaturated, substituted or unsubstituted, and may comprise a catenary heteroatom; each $Z_1$ and $Z_2$ is independently selected from F and $CF_3$; n is 0 or 1; q is 0 or 1; and m is at least 2; and M is a cation; (ii) brominating the sulfinate oligomer according to Formula I; and (iii) introducing an energy source.

Embodiment 11. The method according to embodiment 10, wherein the energy source is added after brominating the sulfinate oligomer.

Embodiment 12. The method according to embodiment 10, wherein the energy source is added during the step of brominating the polysulfinate oligomer.

Embodiment 13. The method according to any one of embodiments 10 to 12, wherein the energy source is selected from the group consisting of: heat, electromagnetic-radiation, and combinations thereof.

Embodiment 14. The method according to any one of embodiments 9 to 13, wherein the brominating step is conducted in the presence of water.

Embodiment 15. The method according to any one of embodiments 9 to 14, wherein a brominating agent used in the brominating step is selected from the group consisting essentially of: diatomic bromine, hypobromite, and combinations thereof.

Embodiment 16. The method according to any one of embodiments 9 to 15, wherein the $X_1$, $X_2$, and $X_3$ are all F, and R is a perfluorinated alkylene.

Embodiment 17. The method according to any one of embodiments 9 to 16, wherein R is selected from: $—(CH_2)_a—$, $—(CF_2)_a—$, $—(CF_2)_a—O—(CF_2)_b—$, $—(CF_2CF(CF_3)O)_a—$ and $—(CF_2)_a—[O—(CF_2)_b]_c—$, $—[(CF_2)_a—O—]_b—[(CF_2)_c—O—]_d$, $—[(CF_2)_a—O—]_b—[(CF_2CF(CF_3)O)_c]_d—$, and combinations thereof, wherein a, b, c, and d are independently at least 1.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: bp=boiling point, g=gram; hr=hour; kPa=kilopascal; mol=mole; ml=milliliter, mm Hg=millimeters of mercury; meq=milliequivalent; N=normal, MW=molecular weight; and ppm=parts per million.

| Material | Description and/or Source |
|---|---|
| | Materials |
| MV4S | $CF_2=CF—O—C_4F_8—SO_2F$, made as described in the Example (section A to C) of U.S. Pat. No. 6,624,328 (Guerra) |
| o-MV4S | $R—[CF_2CF(OC_4F_8SO_2F)]n—R$ where n = 2-6 and R is H, $C_2H_5$ and/or $C_7H_{15}$ |
| o-MV4SO2H | $R—[CF_2CF(OC_4F_8SO_2H)]n—R$ where n = 2-6 and R is H, $C_2H_5$ and/or $C_7H_{15}$ |
| LOPEROX TAEC | t-amyl peroxy 2-ethylhexyl carbonate commercially available from Arkema, Philadelphia, PA. |
| THF | Tetrahydrofuran, commercially available from EMD Chemicals, Inc., Gibbstown, NJ. |
| $ClCH_2CH_2Cl$ | Commercially available from EMD Chemicals, Inc., Gibbstown, NJ. |
| 96% $H_2SO_4$ | Commercially available from J. T. Baker, Mallinckrodt Baker, Inc., Phillipsburg, NJ |
| 30% ammonia water | Commercially available from EMD Chemicals, Inc., Gibbstown, NJ. |
| t-BuOCH$_3$ | Commercially available from EMD Chemicals, Inc., Gibbstown, NJ. |

Preparation of o-MV4S Oligomer 220 g of MV4S was oligomerized in a 500 m mL flask with 20 g "LOPEROX TAEC" peroxide at 110° C. for 4 hrs under nitrogen. An additional 7.01 g "LOPEROX TAEC" was added at 110° C. and reacted for an additional 15 hrs. Distillation was carried out for 2 hrs at 110° C. under full vacuum (<0.5 kPa (4 mm Hg)) to remove unreacted MV4S and low boiling point oligomers to yield 117.1 g o-MV4S oligomer (isolated yield 53%). From $^{19}F$ NMR (fluorine-19 nuclear magnetic resonance), no $CF_2=CF—O—$ was observed in comparison with the $^{19}F$ NMR of the starting material MV4S. Liquid Chromatography-Mass Spectroscopy (LC-MS) analysis results are summarized in Table 1. Relative areas of the LC-MS indicated the general structure $R^1—(CF_2—CF(OCF_2CF_2CF_2CF_2SO_2F))n-R^2$ where n equals 2-6 and $R^1$ and $R^2$ were either H, $C_2H_5$ or $C_7H_{15}$. The average oligomer had 3.2 units.

TABLE 1

| LC-MS for $R^1—(CF_2—CF(OCF_2CF_2CF_2CF_2SO_2F))n—R^2$ | | | | |
|---|---|---|---|---|
| Total % in | $R^1/R^2$ | | $R^1/R^2$ | |
| oligomer | H/$C_7H_{15}$ | MW | H/$C_2H_5$ | MW |
| n = 2   18.00% | 5.40% | 860 | 12.60% | 790 |
| n = 3   54.50% | 11.10% | 1240 | 43.40% | 1170 |
| n = 4   15.40% | 6.30% | 1620 | 9.10% | 1550 |
| n = 5   11.80% | 1.90% | 2000 | 9.90% | 1930 |
| n = 6   0.20% | 0.20% | 2380 | * | 2310 |

* Below detection limit

Preparation of o-MV4SO$_2$H Oligomer 116 g o-MV4S oligomer, prepared as per "PREPARATION OF o-MV4S OLIGOMER", above, was dissolved in 106 g dried THF and added to a dispersion solution of 16.65 g NaBH$_4$ in 300 g dried THF at 20° C. under nitrogen over 2 hrs. The temperature increased to 50° C. due to the exothermic reaction. After the addition the reaction was continued with stirring for 1 hr. $^{19}F$ NMR analysis showed all SO$_2$F had disappeared, and the signal of CF$_2$SO$_2$ was shifted from original –111 ppm (CF$_2$SO$_2$F) to –117 ppm and –128 ppm (CF$_2$SO$_2$M) at the mole ratio of 1 to 1. Upon hydrolysis of the solution with H$_2$SO$_4$—H$_2$O (2N), the signal at –117 ppm disappeared and the signal grew at –128 ppm, indicating the signal at –117 ppm was CF$_2$SO$_2$B. The acidified solution was extracted with t-BuOCH$_3$ and worked up to yield 181.5 g of wet product (theoretical 111.3 g product, indicating purity of 61% in t-BuOCH$_3$—H$_2$O). The $^{19}F$ NMR spectrum confirmed [CF$_2$—CF(OCF$_2$CF$_2$CF$_2$CF$_2$SO$_2$H)]n-(o-MV4SO$_2$H).

Example 1

20 g (61%, 34.5 meq —CF$_2$SO$_2$H) o-MV4SO$_2$H oligomer made as per "PREPARATION OF o-MV4SO2H OLIGOMER" was dissolved in 50 g water, which was neutralized with 4.5% KOH to pH >8. 5.52 g bromine (34.5 mmol) was slowly added at 20° C. with stirring. The red bromine color faded quickly and an additional 1.2 g bromine was added until the red bromine color did not fade. The solution was then reacted at 20° C. for additional hr. After standing, two phases were separated. From $^{19}F$ NMR analysis only the bottom layer showed a fluorine signal. The signal of CF$_2$SO$_2$K at –128 ppm (starting material) had disappeared and new signals at –61 and –101 ppm were found, corresponding to —CF$_2$Br and —CF$_2$SO$_2$Br in a mole ratio of 1 to 1.86. 11.5 g of the brominated oligomer was isolated from the bottom layer.

Example 2

20 g (61%, 34.5 meq —CF$_2$SO$_2$H) o-MV4SO2H oligomer made as per "PREPARATION OF o-MV4SO2H OLIGOMER", above, was dissolved in 50 g water, which was neutralized with 4.5% KOH to pH >8. The solution was cooled with an ice-water bath to 0° C., and 2.5 g bromine was slowly added with stirring. The reaction was slightly exothermic and the red bromine color faded in seconds and the solution became cloudy (likely due to the formation of KBr salt). When the temperature cooled to 0° C. again, 3.0 g additional bromine was added until the red bromine color remained. After reaction at 0° C. for 10 min, the solution was allowed to warm-up to 20° C. $^{19}$F NMR analysis indicated the signal of —CF$_2$SO$_2$K at −128 ppm (starting material) disappeared, and new signals at −61 ppm and −101 ppm appeared, corresponding to —CF$_2$Br and —CF$_2$SO$_2$Br in a mole ratio of 1 to 3.12. A lower reaction temperature thus produced oligomer with less —CF$_2$Br relative to —CF$_2$SO$_2$Br.

An attempt was made to isolate the bottom high viscosity product by extraction with ClCH$_2$CH$_2$Cl, however a stable emulsion formed. Solvent was stripped out by rotary evaporation at 20 to 60° C. yielding 10.2 g of brominated oligomer, which was confirmed by $^{19}$F NMR and LC-MS, indicating the conversion of —CF$_2$SO$_2$Br to —CF$_2$Br during the work-up process.

Example 3

20 g (61%, 34.5 meq —CF$_2$SO$_2$H) o-MV4SO2H oligomer made as per "PREPARATION OF o-MV4SO2H OLIGOMER", above, was dissolved in 50 g water, which was neutralized with 4.5% KOH to pH >8. The solution was cooled with an ice-water bath to 0° C., and 2.5 g bromine (15.6 mmol) was slowly added while stirring. The red bromine color faded in seconds and the reaction was continued at 0° C. for 30 min. $^{19}$F NMR analysis of the solution showed signals of CF$_2$SO$_2$K at −128 ppm (starting material) and a new signal of —CF$_2$SO$_2$Br at −101 ppm in a mole ratio of about 1:1. A small amount (less than 5 mole % versus the desired product) of —CF$_2$Br was identified in the reaction solution.

Example 4

20 g (61%, 34.5 meq —CF$_2$SO$_2$H) o-MV4SO2H oligomer made as per "PREPARATION OF o-MV4SO2H OLIGOMER", above, was dissolved in 50 g water, which was neutralized with 10% ammonia water solution (diluted from commercial 30%) to pH >8. To this solution 3.3 g (20.6 mmol) bromine was added slowly at 20° C. while stirring and the red bromine color faded in seconds. After reaction at 20° C. for 3 hrs $^{19}$F NMR analysis monitoring at 20° C. showed the formation of —CF2Br at −65 ppm with an unreacted signal of —CF$_2$SO$_2$ NH$_4$ at −131 ppm. The reaction was allowed to continue and samples were collected at 8 hours and 24 hours for $^{19}$F NMR analysis. The ratio of —CF$_2$Br/—CF$_2$SO$_2$NH$_4$ determined by $^{19}$F NMR at different times are indicated below:

| Time | Ratio of —CF$_2$Br/—CF$_2$SO$_2$NH$_4$ |
|---|---|
| 3 hrs | 16/84 |
| 8 hrs | 36/64 |
| 24 hrs | 59/41 |

After allowing the reaction to continue for 24, hours, the reaction was acidified with 2 N H$_2$SO$_4$ solution, then extracted with t-BuOMe (3×30 mL). The combined extraction solutions were washed with 0.1 NH$_2$SO$_4$ solution (2×10 mL) and dried over MgSO$_4$. 12.2 g of product was isolated. $^{19}$F NMR indicated —CF$_2$Br/—CF$_2$SO$_2$H in a mole ratio of 59:41.

Example 5

An oligomer was made as in Example 3, but with 2.76 g bromine (17.25 mmol) instead of 2.5 g bromine and the reaction mixture was heated to 60° C. for 30 min. $^{19}$F NMR analysis of the solution indicated no —CF$_2$SO$_2$Br signal at −101 ppm and only signals of —CF$_2$SO$_2$K at −128 ppm and —CF$_2$Br at −60 ppm at the 1:1 mole ratio.

Example 6

An oligomer was made as in Example 3, but with 5.6 g bromine instead of 2.5 g bromine. $^{19}$F NMR analysis indicated all of the —CF$_2$SO$_2$K signal at −128 ppm disappeared and —CF$_2$SO$_2$Br was formed at more than 90% at −101 ppm with a small amount of —CF$_2$Br at −61 ppm. In a NMR tube, the solution was added and irradiated with UV for 30 min (two 15 Watt "GERMICIDAL G15T8" bulbs commercially available from Sylvania, Danvers, Mass.) from a distance of 2 inches (50.8 millimeters). $^{19}$F NMR spectrum showed 100% conversion of —CF$_2$SO$_2$Br to —CF$_2$Br.

Foreseeable modifications and alterations of this invention will be apparent to those skilled in the art without departing from the scope and spirit of this invention. This invention should not be restricted to the embodiments that are set forth in this application for illustrative purposes. To the extent that there is a conflict or discrepancy between this specification and the disclosure in any document incorporated by reference herein, this specification will control.

What is claimed is:

1. A composition comprising an oligomer comprising a repeating unit of:

Formula (II)

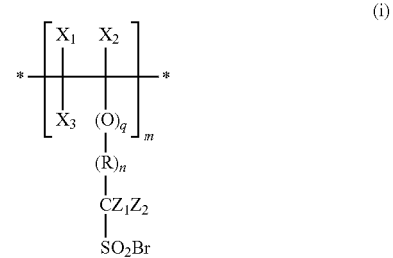

Formula (III)

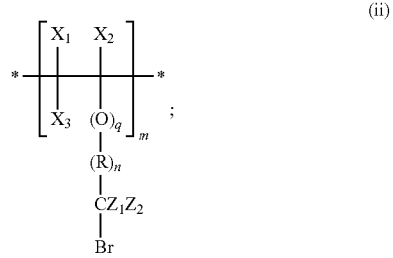

wherein $X_1$, $X_2$, and $X_3$ are each independently selected from F, Cl, H, and CF$_3$; R is a linear or branched linking group, which may be saturated or unsaturated, substituted or unsubstituted, and may comprise a catenary heteroatom; each $Z_1$ and $Z_2$ is independently selected from F and CF$_3$; n is 0 or 1; q is 0 or 1; and m is at least 2 wherein the oligomer has a number average molecular weight of no more than 20,000 grams/mole.

2. The composition of claim 1 further comprising a repeating unit of Formula (IV):

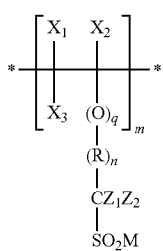

wherein $X_1$, $X_2$, and $X_3$ are each independently selected from F, Cl, H, and $CF_3$; R is a linear or branched linking group, which may be saturated or unsaturated, substituted or unsubstituted, and may comprise a catenary heteroatoms; each $Z_1$ and $Z_2$ is independently selected from F and $CF_3$; q is 0 or 1; n is 0 or 1; and q+n is at least 1; wherein M is a cation and $R_1$ and $R^2$ are independently selected from a linear or branched linking group, which may be saturated or unsaturated, substituted or unsubstituted, and may comprise catenary heteroatoms.

3. The composition according to claim 1, further comprising a repeating unit:

wherein Q is derived from a monomer and p is at least 1.

4. The composition according to claim 3, wherein the monomer is selected from: ethylene, tetrafluoroethylene, propylene, hexafluoropropylene, vinyl chloride, vinyl fluoride, a fluoroalkyl substituted ethylene, vinylidene fluoride, allyl iodide, fluorinated alkyl vinyl ethers, fluorinated alkoxy vinyl ethers, bromotrifluoroethylene, chlorotrifluoroethylene, $CF_3CH=CH_2$, $C_4F_9CH=CH_2$, $CF_3OCF=CF_2$, $C_3F_7OCF=CF_2$, $CF_2=CFOCF_2CF(CF_3)OCF_2CF_2CF_3$, $CF_2=CFOCF_2CF_2CF_2CN$, $CF_2=CFOCF_2CF_2CF_2CO_2CH_3$, $CF_2=CFOCF_2CF(CF_3)OCF_2CF_2CO_2CH_3$, $CF_2=CFOCF_2CF_2CF_2CH_2OH$, and $CF_2=CFOCF_2CF_2CF_2OCF_3$.

5. The composition according to claim 1, wherein the $X_1$, $X_2$, and $X_3$ are all F, n is 1, and R is a perfluorinated alkylene.

6. The composition according to claim 1, wherein R is selected from: $-(CH_2)_a-$, $-(CF_2)_a-$, $-(CF_2)_a-O-(CF_2)_b-$, $-(CF_2CF(CF_3)O)_a-$ and $-(CF_2)_a-[O-(CF_2)_b]_c-$, $-[(CF_2)_a-O]_b-[(CF_2)_c-O]_d-$, $-[(CF_2)_a-O-]_b-[(CF_2CF(CF_3)O)_c-]_d-$, and combinations thereof, wherein a, b, c, and d are each independently at least 1.

7. The composition according to claim 3, wherein the monomer is selected from a non-fluorinated olefin, a partially fluorinated olefin, a perfluorinated olefin, and combinations thereof.

8. The composition according to claim 3, wherein the monomer is selected from the following Formula: $CY_2=CY(R^3)$, wherein each Y is independently selected from H, Cl or F ; and $R^3$ is selected from I, Br, $O-R_f-U$ and $R_f-U$ wherein U=I, F, H, Br, $CH_2OH$, $CO_2R^1$, CN, $C(O)NR^1R^2$, $P(O)(OR^1)_2$, $OR^1$, $OCF_3$ or $OC_3F_7$, and $R_f$ is a perfluorinated or partially fluorinated alkylene group optionally containing O atoms.

9. The composition according to claim 1, wherein the oligomer is a liquid.

* * * * *